(12) United States Patent
Muderlak

(10) Patent No.: US 11,089,915 B2
(45) Date of Patent: Aug. 17, 2021

(54) DISPENSER FOR USE WITH REFILL CARTRIDGE

(71) Applicant: Xela Innovations, LLC, Glendale, WI (US)

(72) Inventor: Todd J. Muderlak, Whitefish Bay, WI (US)

(73) Assignee: XELA Innovations, LLC, Glendale, WI (US)

( * ) Notice: Subject to any disclaimer, the term of this patent is extended or adjusted under 35 U.S.C. 154(b) by 0 days.

(21) Appl. No.: 16/664,148

(22) Filed: Oct. 25, 2019

(65) Prior Publication Data

US 2021/0121024 A1   Apr. 29, 2021

(51) Int. Cl.
*A47K 5/12* (2006.01)

(52) U.S. Cl.
CPC .................... *A47K 5/1217* (2013.01)

(58) Field of Classification Search
CPC ......... A47K 5/1217; A61L 9/12; A61L 9/305; A61L 9/307
USPC .......... 222/23, 41, 181.3, 187; 239/326, 387
See application file for complete search history.

(56) References Cited

U.S. PATENT DOCUMENTS

| | | |
|---|---|---|
| 4,166,087 A | 8/1979 | Cline et al. |
| 4,383,951 A | 5/1983 | Palson |
| 4,931,258 A | 6/1990 | Zlotnik et al. |
| 5,114,625 A | 5/1992 | Gibson |
| 5,249,718 A | 10/1993 | Muderlak |
| 5,297,734 A | 3/1994 | Toda |
| 5,449,117 A | 9/1995 | Muderlak et al. |
| 5,657,926 A | 8/1997 | Toda |
| 5,673,825 A | 10/1997 | Chen |
| 6,039,212 A | 3/2000 | Singh |
| 6,293,474 B1 | 9/2001 | Helf et al. |
| 6,341,732 B1 | 1/2002 | Martin et al. |
| 6,450,419 B1* | 9/2002 | Martens, III .......... A01M 1/205 239/102.1 |

(Continued)

FOREIGN PATENT DOCUMENTS

| | | |
|---|---|---|
| DE | 9402313 | 3/1994 |
| EP | 0365770 | 5/1990 |

(Continued)

OTHER PUBLICATIONS

PCT/US2019/058171 International Search Report and Written Opinion of the International Searching Authority dated Jul. 22, 2020 (14 pages).

*Primary Examiner* — Lien M Ngo
(74) *Attorney, Agent, or Firm* — SmithAmundsen LLC

(57) ABSTRACT

Dispensers of the present technology are configured to receive a replaceable refill cartridge, and may include a back housing, a front cover, a control unit, a refill housing configured to receive a refill cartridge, and a switch board positioned between the refill housing and the back housing. Dispensers may also include at least one refill guide removably connected to the refill housing. The switch board may include at least one switch operatively connected to the control unit. The at least one switch may be a refill recognition switch configured to send at least a refill recognition signal to the control unit indicating that a refill cartridge is present in the refill housing, or a refill size switch configured to send a refill size signal to the control unit indicating a size of the refill cartridge.

18 Claims, 12 Drawing Sheets

(56) References Cited

U.S. PATENT DOCUMENTS

| | | | |
|---|---|---|---|
| 7,157,057 B2 | 1/2007 | Gohil | |
| 7,244,398 B2 | 7/2007 | Kotary et al. | |
| 7,389,943 B2 * | 6/2008 | Jaworski | A01M 1/205 239/102.2 |
| 7,469,844 B2 * | 12/2008 | Conway | B05B 17/0607 239/102.2 |
| 7,691,336 B2 * | 4/2010 | Westring | A61L 9/04 422/125 |
| 7,922,104 B2 | 4/2011 | Zlotnik et al. | |
| 8,157,188 B2 | 4/2012 | Duston et al. | |
| 8,889,082 B2 | 11/2014 | Muderlak et al. | |
| 8,931,713 B2 | 1/2015 | Muderlak et al. | |
| 9,827,343 B2 * | 11/2017 | Lima | H05B 1/0252 |
| 2004/0226962 A1 | 11/2004 | Mazursky et al. | |
| 2004/0265189 A1 | 12/2004 | Schwarz | |
| 2005/0002834 A1 | 1/2005 | Gohil | |
| 2005/0087260 A1 | 4/2005 | Marszalec et al. | |
| 2005/0285538 A1 | 12/2005 | Jaworski et al. | |
| 2006/0163376 A1 | 7/2006 | Lakatos et al. | |
| 2006/0180143 A1 | 8/2006 | Lind et al. | |
| 2007/0036673 A1 | 2/2007 | Selander | |
| 2007/0235555 A1 | 10/2007 | Helf et al. | |
| 2008/0060119 A1 | 3/2008 | Pinizzotto | |
| 2008/0173705 A1 | 7/2008 | Girard et al. | |
| 2009/0151061 A1 | 6/2009 | Chen | |
| 2010/0147972 A1 | 6/2010 | Lakatos et al. | |
| 2012/0187217 A1 * | 7/2012 | Maget | A61L 9/127 239/326 |
| 2013/0034444 A1 | 2/2013 | Muderlak et al. | |
| 2014/0064713 A1 * | 3/2014 | Niemiec | A61L 9/035 392/387 |
| 2018/0043048 A1 | 2/2018 | Sidawi et al. | |
| 2018/0304288 A1 * | 10/2018 | Casper | B05B 9/043 |

FOREIGN PATENT DOCUMENTS

| | | |
|---|---|---|
| EP | 2113259 | 11/2009 |
| EP | 2564878 | 3/2013 |
| WO | 2012/175972 | 12/2012 |
| WO | 2013/063690 | 5/2013 |

* cited by examiner

DISPENSER FOR USE WITH REFILL CARTRIDGE

FIELD OF THE INVENTION

The present technology relates to dispensers and, more particularly, to dispensers for use with a replaceable refill cartridge.

DESCRIPTION OF RELATED ART

Dispensers of various types for dispensing substances such as cleansers, lotions, soaps, sanitizers, fragrances, and other items have become popular, especially in the area of hygiene. For example, battery-operated, metered aerosol fragrance dispensers have become popular in commercial settings such as public and office restrooms and other commercial room locations. Such devices typically include a DC electric motor, a gear drive operated by the motor which actuates the spray valve, an aerosol fragrance canister, and a programmable timer for adjusting the time interval between sprays.

One problem associated with such motor-operated fragrance dispensers is that the moving mechanical parts tend to increase manufacturing costs, and the components are likely to fail over time. A simpler, more durable solution employs a micro-perforated plate secured to a piezoelectric vibrator that is energized by a power source. Such devices have been used in humidifiers and fragrance dispensers.

SUMMARY

Dispensers of the present technology are configured to receive a replaceable refill cartridge and dispense the contents of the refill cartridge therefrom. The dispensers may be configured to dispense cleanser, lotion, soap, sanitizer, fragrance, or any other suitable substance. The substance to be dispensed may be in a liquid form, or any other suitable form, such as gel, wicks, or impregnated plastics. The dispensing mechanism may be any suitable dispensing mechanism, including but not limited to pumps or fans, and in some examples may include a piezoelectric nozzle.

Dispensers according to certain examples described herein may include a back housing, and a front cover connected to the back housing, wherein the front cover has an open position and a closed position relative to the back housing. Dispensers may include a power and control unit connected to the back housing, the power and control unit comprising at least a control unit. Dispensers may include a refill housing connected to the back housing, the refill housing being configured to receive a refill cartridge. Dispensers may include a switch board positioned between the refill housing and the back housing, the switch board comprising at least one switch operatively connected to the control unit.

In some examples, dispensers also include at least one refill guide removably connected to the refill housing.

In some examples, the switch board may include a first switch operatively connected to the control unit and a second switch operatively connected to the control unit. The first switch may be a refill recognition switch configured to send to the control unit at least one of a new refill signal indicating that a new refill has been inserted into the dispenser, and a refill recognition signal indicating that a refill cartridge is present in the refill housing. The second switch may be a refill size switch configured to send a refill size signal to the control unit indicating a size of the refill cartridge.

In some examples, the control unit may include at least one processor and at least one non-volatile memory, and the at least one non-volatile memory may store a dispenser control algorithm that, when executed by the at least one processor, causes the control unit to control operation of the dispenser. The control algorithm may cause the control unit to control operation of the dispenser according to the following steps: determining whether a refill cartridge is present; determining a size of the refill cartridge if the refill cartridge is present, wherein the size of the refill cartridge may be a first size or a second size; executing a set of default settings, wherein the set of default settings is a first set of default settings when the refill cartridge has the first size and a second set of default settings when the refill cartridge has the second size; and causing the dispenser to dispense fragrance. Optionally, a user may input one or more control settings, and the control algorithm may cause the control unit to perform a step of modifying the set of default settings to create a modified set of default settings based on the set of default settings and user input control settings, and then causing the dispenser to dispense substance based on the modified set of default settings.

BRIEF DESCRIPTION OF THE DRAWINGS

Specific examples have been chosen for purposes of illustration and description, and are shown in the accompanying drawings, forming a part of the specification. Within the Figures, like parts have been given like numbers for ease of reference. It should be understood that the drawings are not necessarily drawn to scale and that they are intended to be merely illustrative.

DETAILED DESCRIPTION

FIGS. 1-10 illustrate one example of a dispenser 100 of the present technology. While the illustrated example is configured as a fragrance dispenser, it should be understood that other examples may be configured to dispense other substances. Additionally, while the illustrated example shows a refill cartridge that has a piezoelectric nozzle, it should be understood that other examples may be configured to dispense substance using other dispensing mechanisms.

Figure 1:
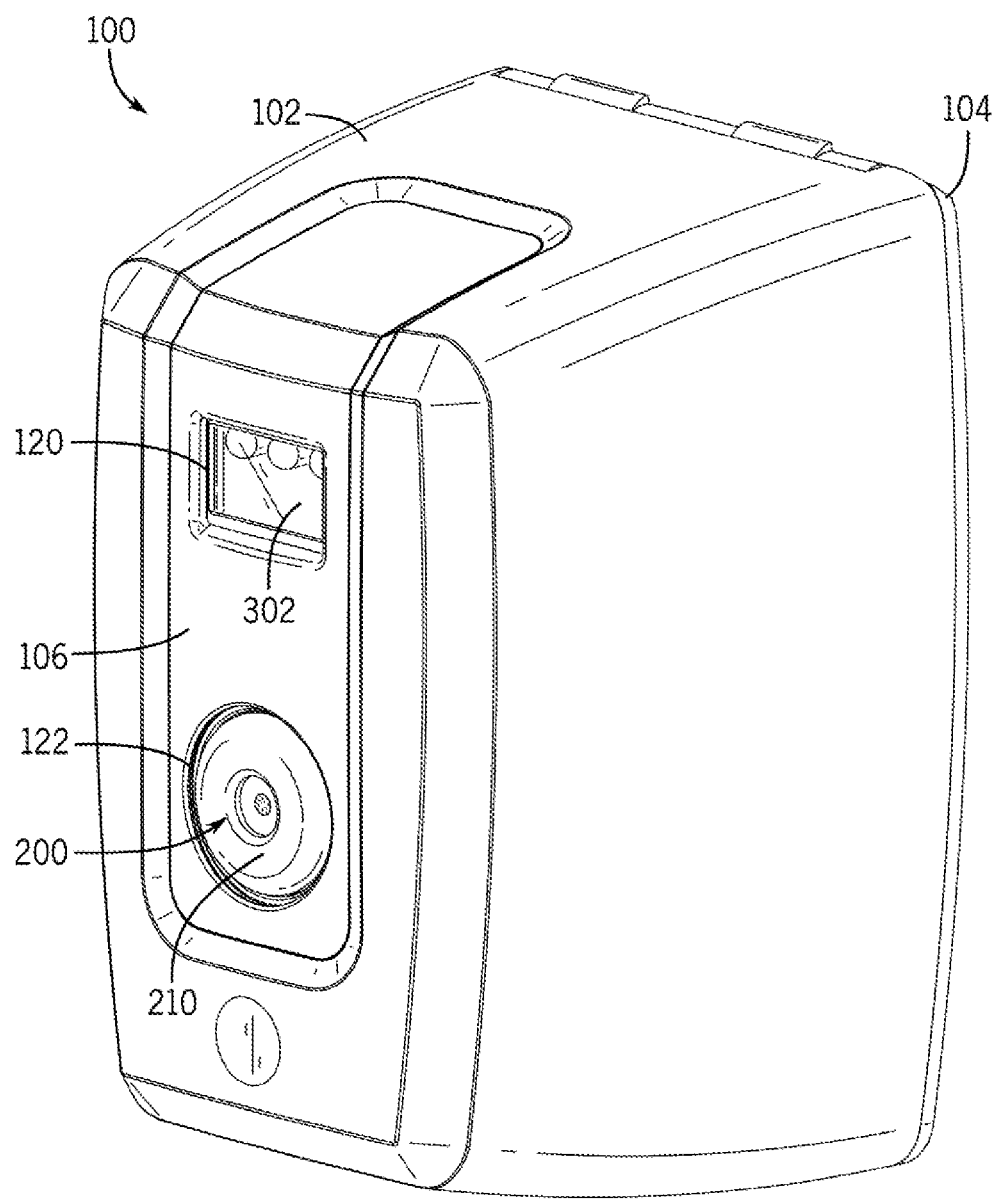
FIG. 1 is a perspective view of one example of a dispenser of the present technology.

Referring to FIG. 1, the dispenser 100 incudes a front cover 102 and a back housing 104 that are configured to receive and hold a refill cartridge 200. The dispenser 100 has a closed position, as shown in FIG. 1, which is the position in which the dispenser 100 operates, dispensing substance from the refill cartridge 200. In this example, the dispenser may dispense fragrance from the refill cartridge 200 into the air. The dispenser 100 may be configured to be mounted to a wall by securing the back housing 104 to the wall. Alternatively, the dispenser 100 may be configured as a free standing device, or be provided with or attach to a stand.

Figure 2:
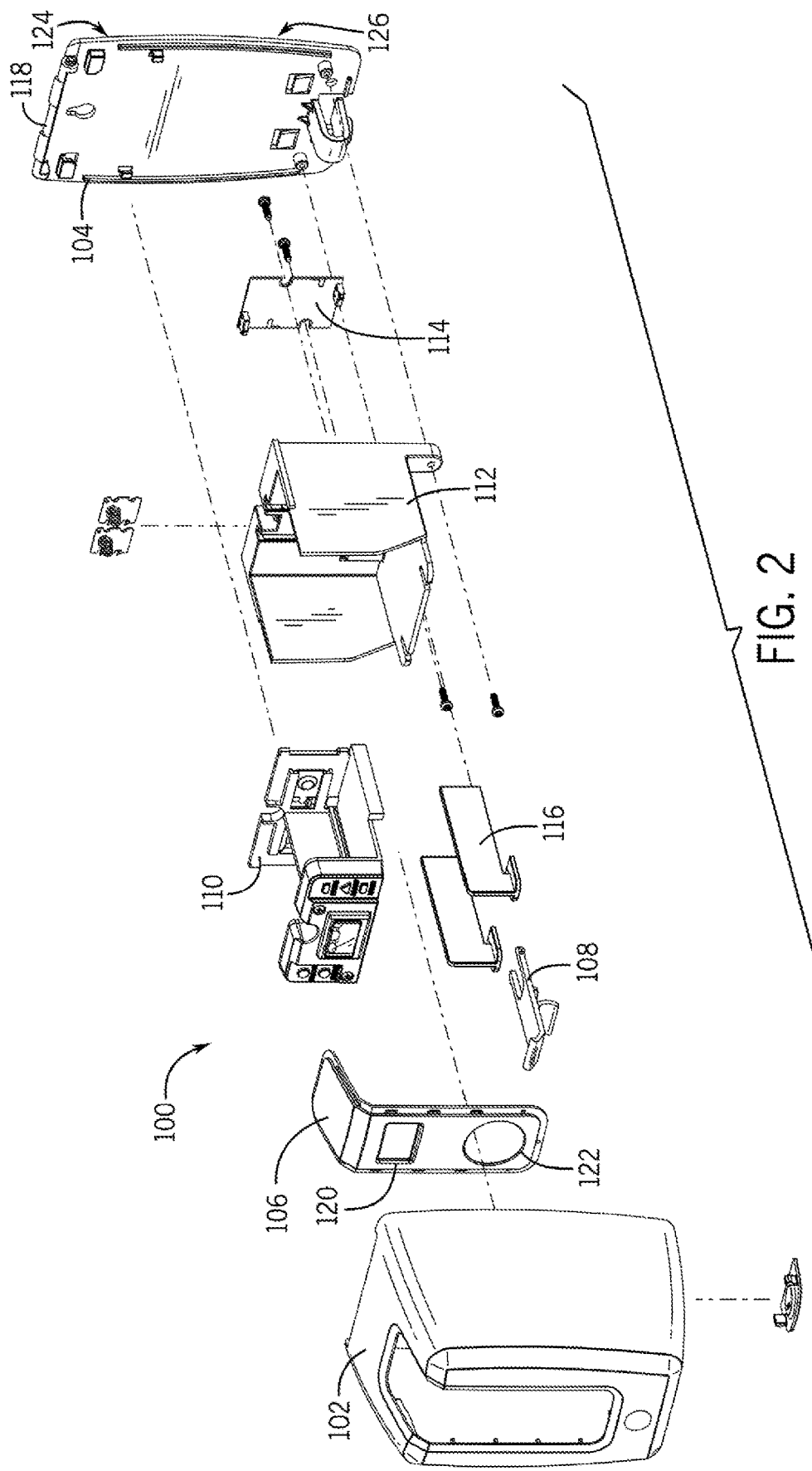
FIG. 2 is an exploded view of the dispenser of FIG. 1.

Referring to FIG. 2, the dispenser 100 incudes a front cover 102, back housing 104, lens 106, refill lock 108, power and control unit 110, refill housing 112, switch board 114, and refill guides 116. Generally, the front cover 102, lens 106, refill lock 108, power and control unit 110, refill housing 112, switch board 114, and refill guides 116 interconnect with each other and the back housing 104 to form the dispenser 100. It should be understood that connections between components as described herein may be direct or indirect.

The front cover 102 may be connected to the back housing such that the front cover has an open position and a closed position relative to the back housing. In the illustrated example, the front cover 102 is rotatably connected to the back housing 104 by hinge 118. Hinge 118 allows the front cover 102 to be rotated upwardly to an open position of the dispenser 100, or downwardly from the open position to the closed position illustrated in FIG. 1. Hinge 118 may be a friction hinge, which may allow the front cover 102 to remain in the open position without being held open by the user. In other embodiments, the front cover may be connected to the back housing in other ways, such as being slidably connected, or being connected by one or more fasteners. In its open position, the front cover 102 may remain connected at least partially to the back housing, or may be removed from the back housing.

The lens 106 is connected to the front cover. The lens 106 may be removably or permanently connected to the front cover 102, and may in some examples by integrally formed with the front cover 102. The lens 106 may include a control port 120 and a refill cartridge port 122. When the front cover 102 is in the closed position, the control display 302 of the power and control unit 110 may align with and be accessible via the control port 120, as shown in FIG. 1. As also shown in FIG. 1, when a refill cartridge is present and the front cover 102 is in the closed position, at least a portion of the dispenser nozzle 210 of the refill cartridge 200 may extend through the refill cartridge port 122.

The power and control unit 110 may be connected to the back housing 104. In the illustrated embodiment, the power and control unit 110 is shown as being connected to an upper portion 124 of the back housing 104.

Figure 3:
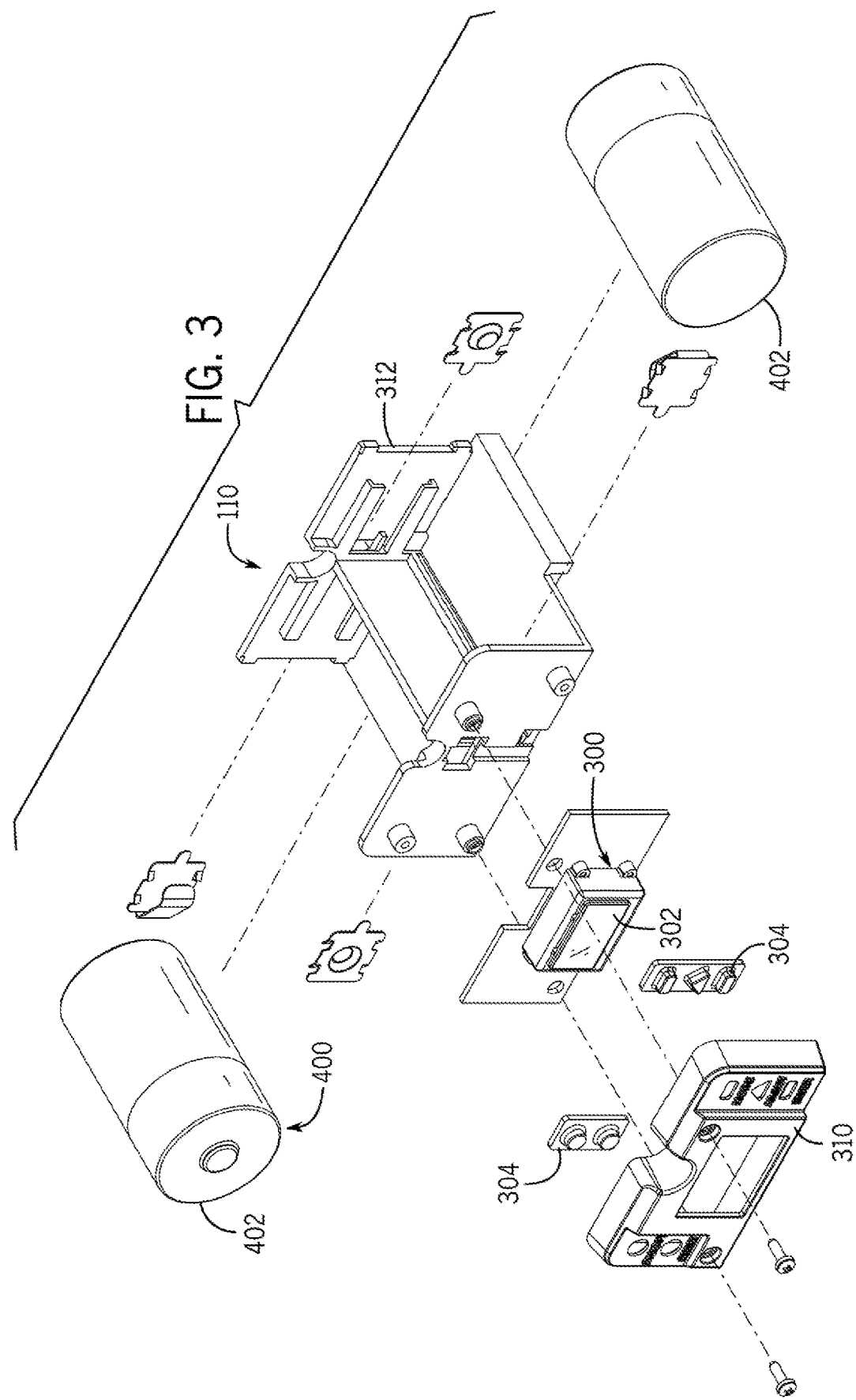
FIG. 3 is an exploded view of the control unit of the dispenser of FIG. 1.
Figure 4:
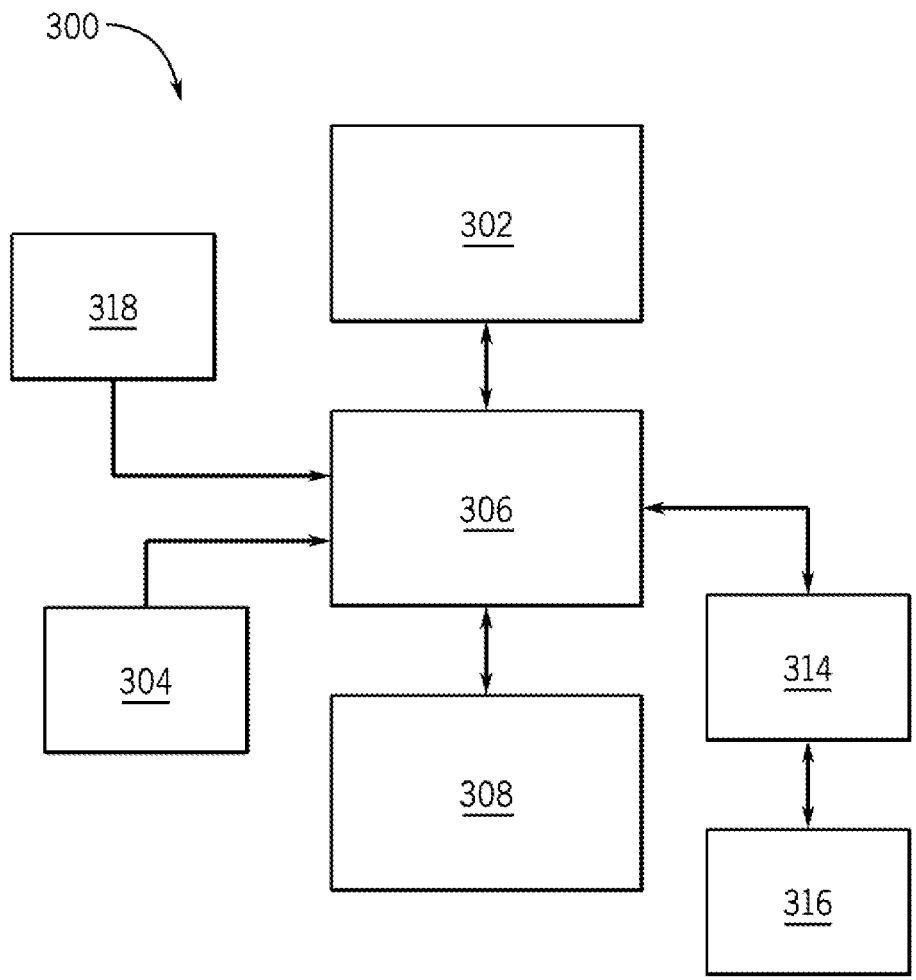
FIG. 4 is a block diagram of the control unit of the dispenser of FIG. 1.

Referring to FIGS. 3 and 4, the power and control unit 110 may include a control unit 300 having a control display 302. The control display 302 displays control setting information to a user, and may include one or more indicators, such as LEDs, or an LCD screen, or any other suitable type of display. The control display 302 may be a touch screen that can receive control setting input from a user. In the illustrated embodiment, the control unit 300 also includes one or more actuators 304, which are illustrated as being push buttons, but may also be any other suitable type of actuator, including but not limited to switches, microswitches, pen-tiometers, or other actuators. The one or more actuators may receive control setting input from a user. Thus, a user may use the one or more actuators to provide control setting input to the control unit 300, such as entering or changing one or more control settings.

Referring to FIG. 4, the control unit 300 may further include at least one processor 306 and at least one non-volatile memory 308. The at least one non-volatile memory 308 receives and stores a dispenser control algorithm, such as control algorithm 600 discussed more fully below, which, when executed by the at least one processor 306, causes the control unit 300 to control the operation of the dispenser 100.

In some embodiments, the control unit 300 may be configured to send and receive signals to and from a user's personal computing device, such as a cell phone, laptop, tablet, desk top computer, or any other personal computing device, via a wired or wireless connection, such as the Internet. For example, the control unit 300 may include a transceiver 314 that can send and receive signals from a user's personal computing device 316. In such an example, the user may be able to use their personal computing device to provide control input to the control unit 300, such as entering or changing one or more control settings. The control unit 300 may thus receive control setting input from the user through the user's personal computing device 316. The control unit 300 may also send signals through transceiver 314 to the user's personal computing device 316, which cause the user's personal computing device 316 to display information about the status and operation of the dispenser. In examples where multiple dispensers 100 are in use, a user may be able to use the user's personal computing device 316 to selectively send and receive signals from each dispenser 100 individually, or all of the dispensers 100 collectively.

Referring back to FIG. 3, the control and power unit 110 may also include a control unit cover 310 and a power source housing 312. The control unit cover 310 may connect to and cover at least portions of the control unit 300. The power source housing 312 is configured to receive and retain at least one power source 400. The illustrated power source consists of one or more batteries 402, which may be rechargeable, but the power source may be any other suitable power source, including but not limited to AC power, or solar power. The control and power unit 110 may be configured to allow the power source to be operatively connected to the control unit 300, to provide power thereto. In alterative embodiments, the power source may be electricity from an electrical socket, rather than a power source internally stored within the dispenser.

Referring back to FIG. 2, the refill housing 112 of the dispenser 100 may be connected to the back housing 104. In the illustrated embodiment, the refill housing 112 is shown as being connected to a lower portion 126 of the back housing 104. The refill housing 112 may be configured to receive a refill cartridge 200. Refill cartridge 200 may be a first refill cartridge 202 having a first size or a second refill cartridge 204 having a second size that differs from the first size. For example, referring to FIGS. 5 and 8, the first refill cartridge 202 may be a small refill cartridge, and the second refill cartridge 204 may be a large refill cartridge. References to small and large herein may refer to the volume of the substance to be dispensed, as well as or as an alternative to the physical size of the refill cartridge 200. For example, a small refill cartridge may contain less liquid fragrance than the large refill cartridge, and be intended to operate during a shorter time period, such as 30 days or 60 days, as compared to 90 days or 120 days for the large refill cartridge. It should be understood that, while two sizes of refill cartridge are described herein, dispensers of the present technology may be configured to accommodate dispensers of several different sizes.

The refill lock 108 may be connected to the refill housing 112. The refill lock 108 may have an engaged positon, and may configured to contact at least a portion of a refill cartridge 200 when in the engaged position.

Figure 5:
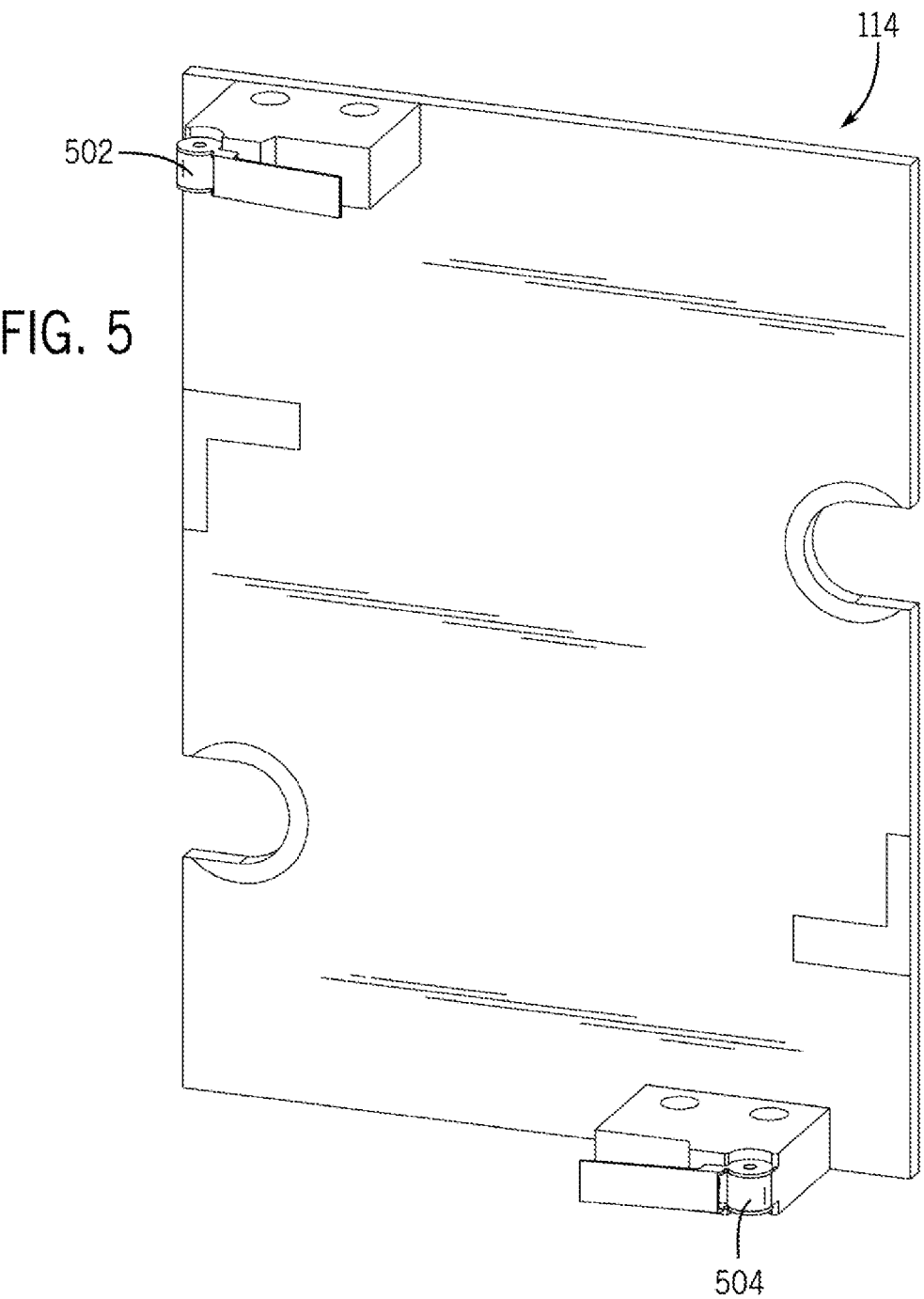
FIG. 5 is a perspective view of a switch board of the dispenser of FIG. 1.

The switch board 114 may be positioned between the refill housing 112 and the back housing 104, and may be directly connected to either the refill housing 112 or the back housing 104. Referring to FIG. 5, the switch board 114 incudes at least one switch 500 operatively connected to the control unit 300. The illustrated embodiment includes two switches, each being operatively connected to the control unit 300. The first switch is a refill recognition switch 502, which is configured to send a refill recognition signal to the control unit indicating that a refill cartridge 200 is present in the refill housing. In at least some embodiments, the refill recognition switch 502 may be activated when it is in contact with a feature on the refill cartridge 200. As long as the refill recognition switch 502 remains activated, it may send a refill recognition signal to the control unit indicating that a refill cartridge 200 is present in the refill housing. Additionally, initial activation of the refill recognition switch 502, or a reactivation after deactivation of the refill recognition switch 502, may send a new refill signal to the control unit, indicating that a new refill has been inserted into the dispenser 100. The second switch shown is a refill size switch 504, which is configured to send a refill size signal to the control unit indicating the size of the refill cartridge. In some embodiments, when the presence of a refill cartridge 200 is indicated by the refill recognition switch 502, a first refill cartridge 202 of a first size is indicated when the refill size switch 504 is activated, and a second refill cartridge 204 is indicated when the refill size switch 504 is not activated.

The dispenser may be configurable to receive at least either the first refill cartridge 202 or the second refill cartridge 204. For example, the illustrated embodiment may include at least one refill guide 116 removably connected to the refill housing 112. As shown, there are two refill guides 116, and each refill guide 116 may be slidably connected to the refill housing 112, or removed from the refill housing 112. The refill housing 112 may be configurable to receive either the first refill cartridge 202 having a first size or the second refill cartridge 204 having a second size based upon the placement of the at least one refill guide 116.

Figure 6:
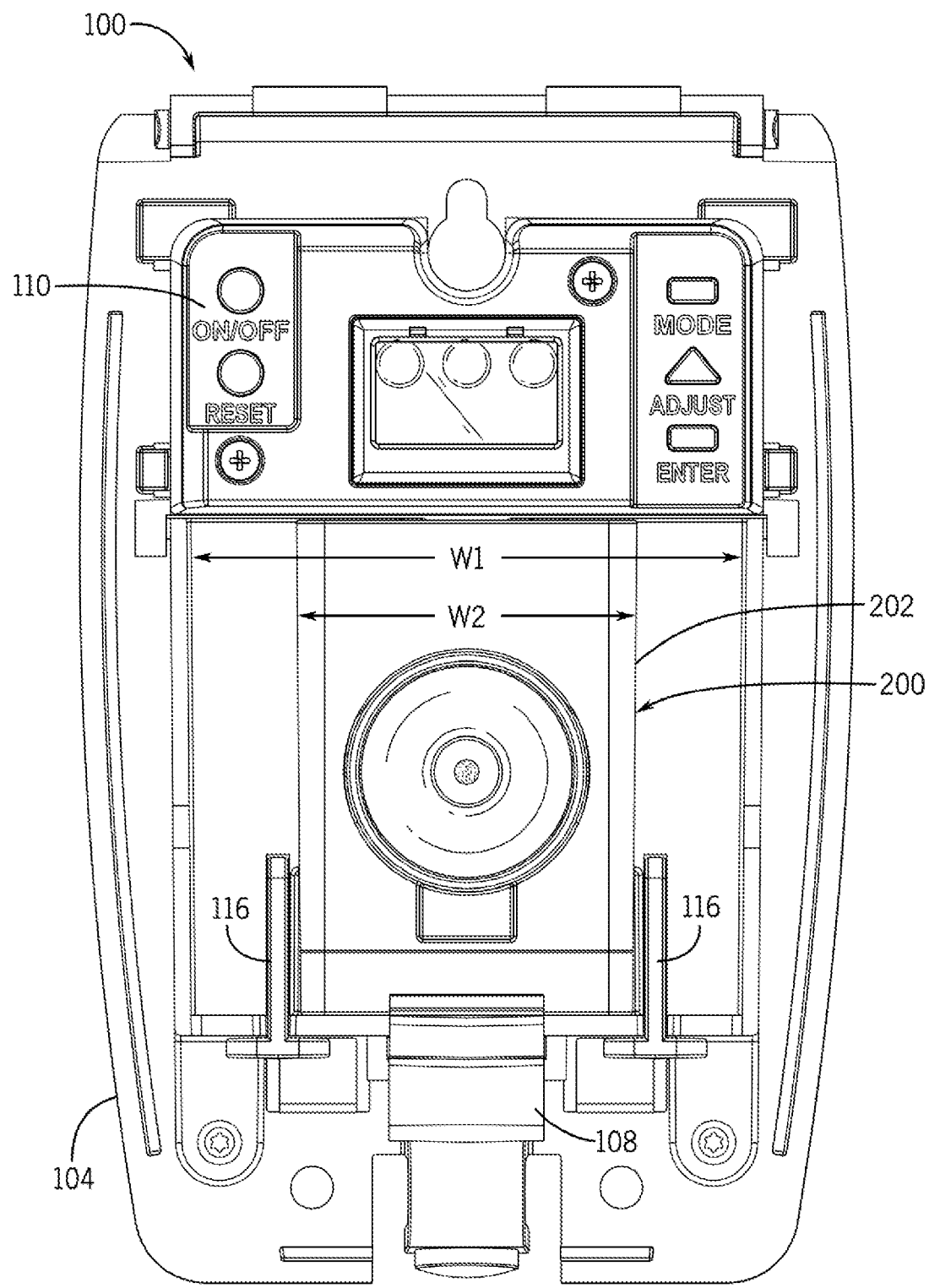
FIG. 6 is a front view of the dispenser of FIG. 1, with a small refill cartridge inserted therein.
Figure 7:
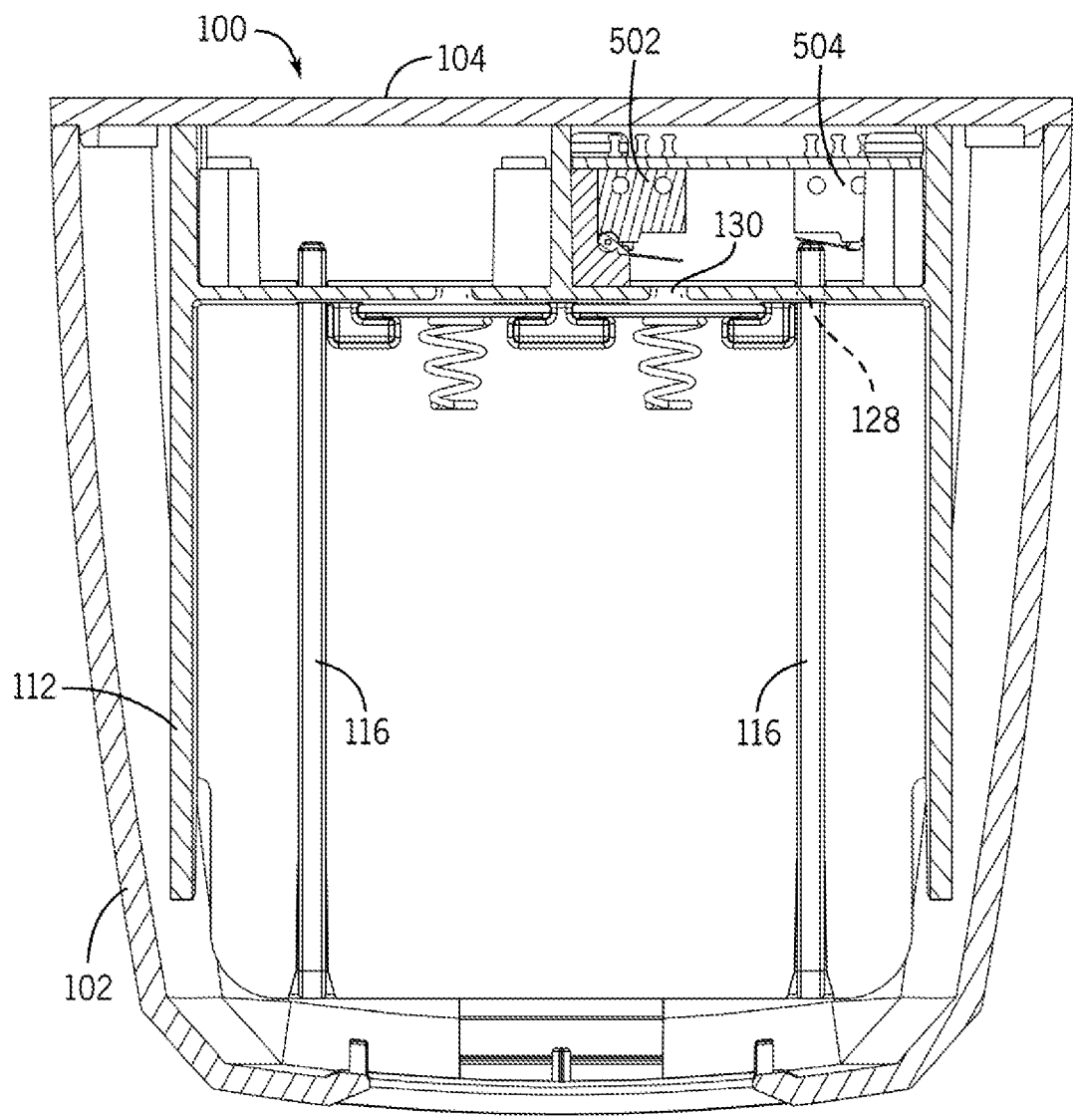
FIG. 7 is a top cross-sectional view of the dispenser of FIG. 1, with refill guides for a small refill cartridge inserted therein, prior to insertion of a small refill cartridge.
Figure 8:
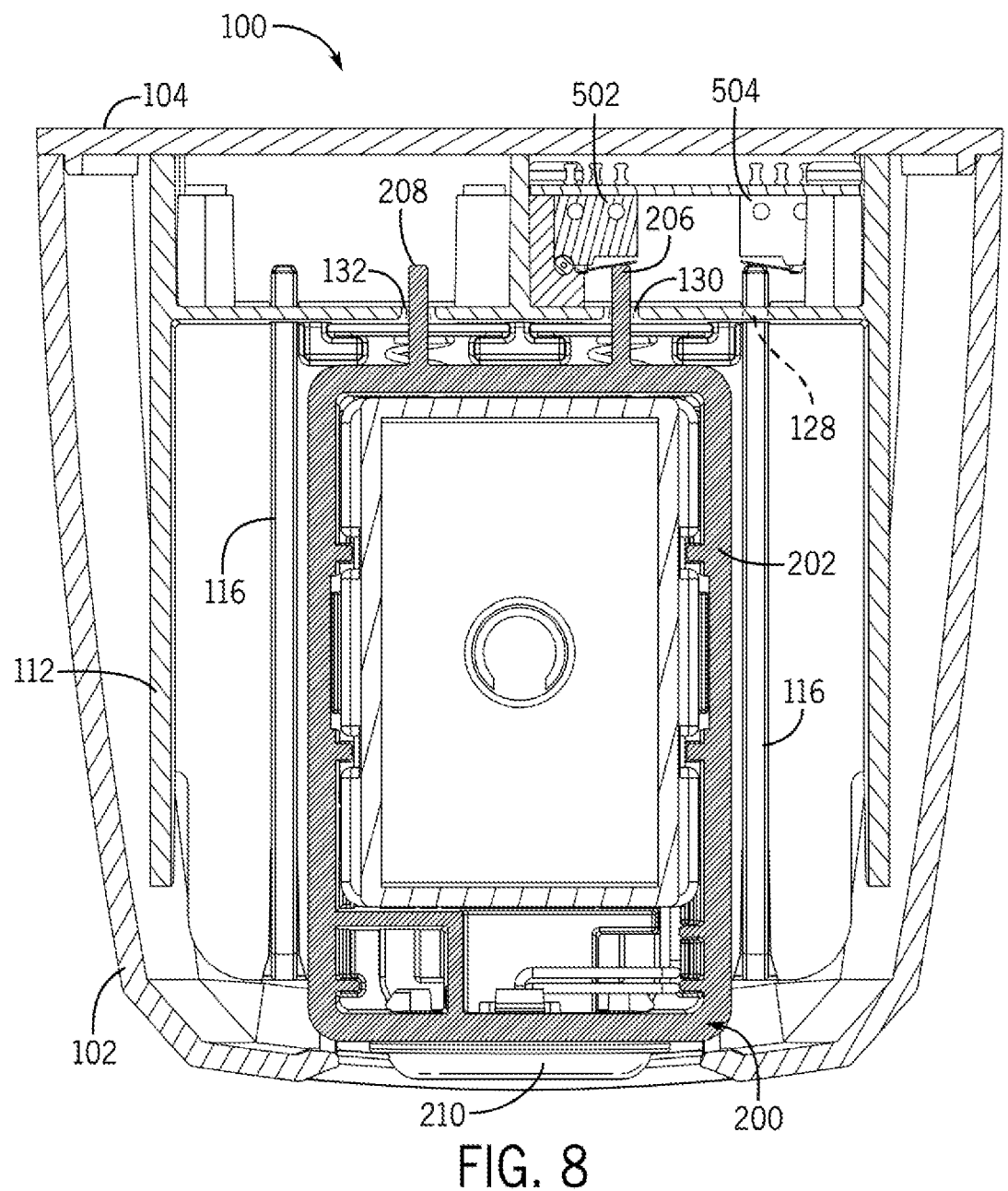
FIG. 8 is a top cross-sectional view of the dispenser of FIG. 1, with a small refill cartridge inserted therein.

FIGS. 6-8 illustrate one example of a first configuration of the dispenser 100, which can be used with a refill cartridge 200 that is a first refill cartridge 202 having a first size that is small. As shown, the refill housing has a width W1 that is larger than the width W2 of the first refill cartridge 202. In order to align the first refill cartridge 202 within the refill housing, each refill guide 116 may be slidably connected to the refill housing, such that it is in an engaged position. At least one refill guide 116 may activate the refill size switch when the refill guide 116 is in the engaged position. For example, as shown in FIGS. 7-8, the refill housing 112 may have a refill guide opening 128 that is aligned with the refill size switch 504, and the at least one refill guide 116 may have an engaged position in which it extends through the refill guide opening 128 in the refill housing 112 and activates the refill size switch 504. Once activated, the refill size switch 504 may send a refill size signal to the control unit 300 indicating that the refill cartridge 200 is a first refill cartridge 202 that has a small size.

The at least one refill guide 116 may also be configured to retain the first refill cartridge 202 when the refill cartridge is placed into the refill housing 112. For example, in the illustrated embodiment, there are two refill guides 116, and the first refill cartridge 202 may be placed into the refill housing 112 between the two refill guides 116.

The first refill cartridge 202 may have a placed position in which the first refill cartridge 202 activates the refill recognition switch 502. For example, as shown in FIG. 8, the first refill cartridge 202 may include at least a first protrusion 206, and the first protrusion 206 of the first refill cartridge 202 may be configured to activate the refill recognition switch 502 when the first refill cartridge 202 is in the placed position. More specifically, the refill housing 112 is shown as having a refill recognition opening 130 that is aligned with the refill recognition switch 502, and the first protrusion 206 of the first refill cartridge 202 extends through the refill recognition opening 130 in the refill housing 112 and activates the refill recognition switch 502 when the first refill cartridge 202 is in the placed positon.

Figure 9:
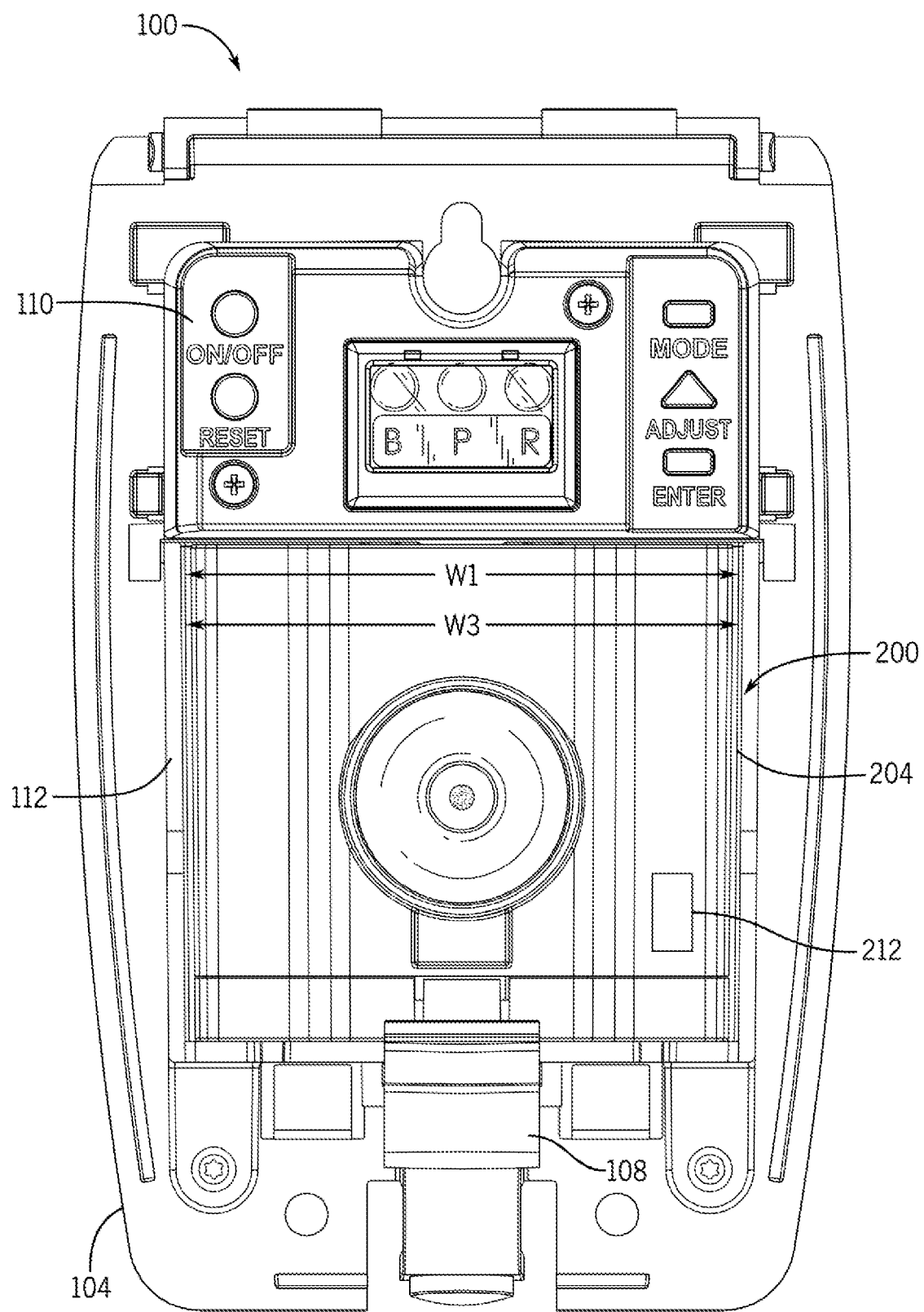
FIG. 9 is a front view of the dispenser of FIG. 1, with a large refill cartridge inserted therein.
Figure 10:
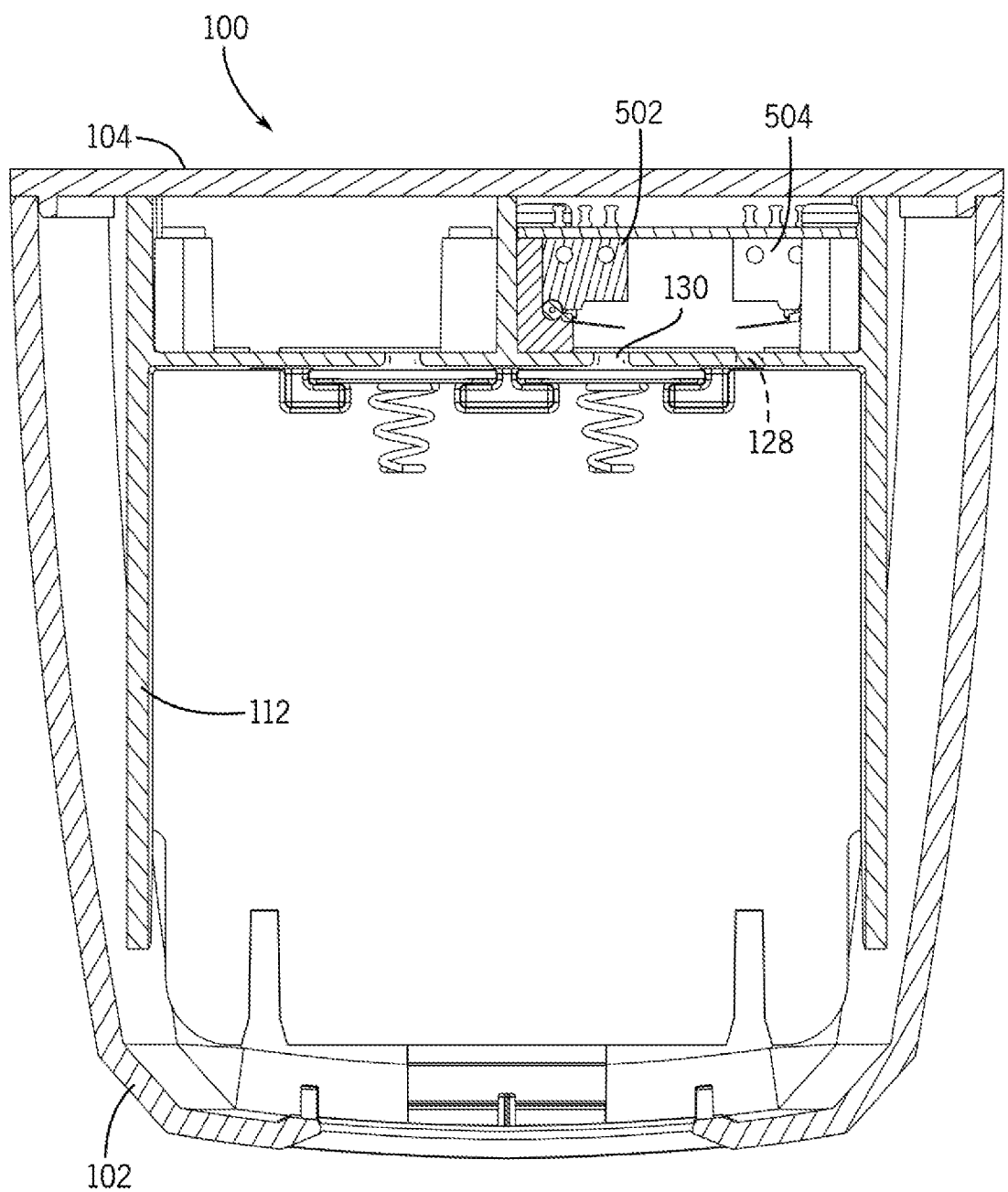
FIG. 10 is a top cross-sectional view of the dispenser of FIG. 1, prior to insertion of a large refill cartridge.
Figure 11:
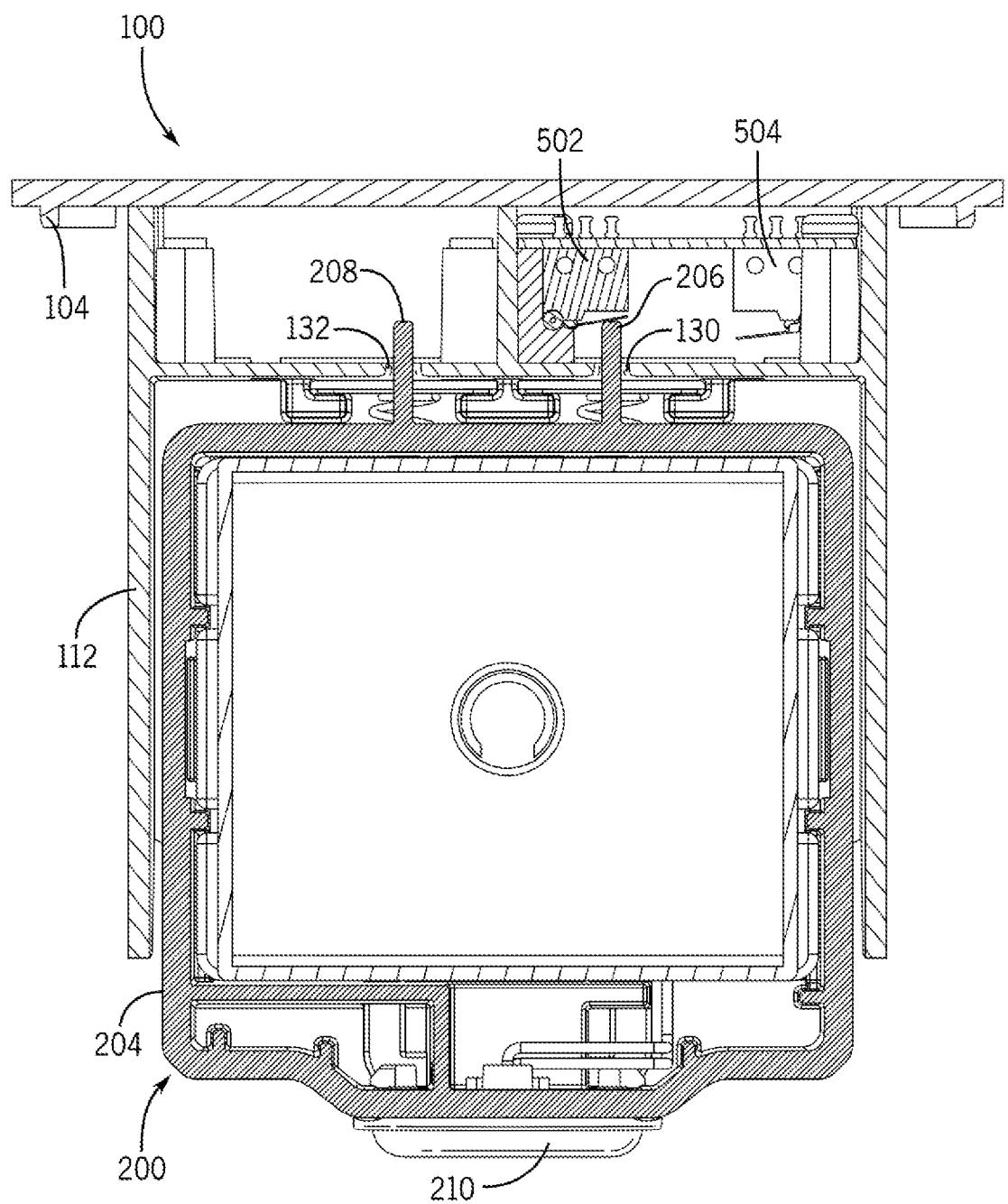
FIG. 11 is a top cross-sectional view of the dispenser of FIG. 1, with a large refill cartridge inserted therein.

FIGS. 9-11 illustrate one example of a second configuration of the dispenser 100, which can be used with a refill cartridge 200 that is a second refill cartridge 204 having a second size that is large. As shown, the refill cartridge 204 has a width W3 that is the same as, or substantially the same as the width W1 of the refill housing. Accordingly, the at least one refill guide 116 may not be needed, and can be in a disengaged position, such as being removed from the refill housing 112.

As with the small first refill cartridge 202, the large refill cartridge 204 may have a placed position in which the refill cartridge 204 activates the refill recognition switch 502. For example, as shown in FIG. 11, the refill cartridge 204 may include a protrusion 206, and the protrusion 206 of the refill cartridge 204 may activate the refill recognition switch 502 when the refill cartridge 204 is in the placed position. More specifically, the refill housing 112 is shown as having a refill recognition opening 130 that is aligned with the refill recognition switch 502, and the protrusion 206 of the refill cartridge 204 extends through the refill recognition opening 130 in the refill housing 112 and activates the refill recognition switch 502 when the refill cartridge 204 is in the placed positon.

In this second configuration, the refill housing 112 may still have a refill guide opening 128 that is aligned with the refill size switch 504, but as can be seen in FIG. 11, the refill size switch is not activated when the refill cartridge is placed in the refill housing 112. The refill size switch 504 thus may not send a refill size signal to the control unit 300, and the absence of the signal may indicate that the refill cartridge 200 is a second refill cartridge 204 that has a large size. Alternatively, when the refill recognition switch is activated by the refill cartridge 204, the control unit 300 may receive the refill recognition signal and then query the refill size switch 504. Because the refill size switch 504 is not activated, the refill size switch 504 may send a refill size signal indicating that the refill cartridge 200 is a second refill cartridge 204 having a large size.

In some embodiments, dispensers of the present technology may also include one or more lock-out features. A lock-out feature may be physical, or electronic. One example of a physical lock-out feature is shown in FIGS. 8 and 11, where the refill cartridge 200 may include at least a second protrusion 208. The refill housing 112 may include a lock-out opening 132, and the second protrusion 208 of the refill cartridge 200 may align with and extend through the lock-out opening 132 in the refill housing 112 when the refill cartridge 200 is in the placed positon. The second protrusion 208 and lock-out opening 132 can be configured, with respect to at least location, size, and shape, to provide customized lock-out features for various embodiments. Physical lock-out features may prevent an unauthorized refill cartridge from fitting properly in the refill housing 112, which may prevent the dispensers from functioning with the unauthorized refill cartridge.

Alternatively, referring to FIG. 11, the refill cartridge 200 may include an electronic lock-out feature 212, such as an RFID tag, or other feature that may be scanned or otherwise detected by the dispenser 100. For example, referring to FIG. 4, the power and control unit 300 may further include a detector 318, which may detect a lock-out feature 212 on the refill cartridge 200 and send an authorization signal to the processor 306 indicating that the refill cartridge 200 is authorized. If a refill is placed that does not have the lock-out feature, the authorization signal sent by the detector 318 may send an authorization signal indicating that the refill cartridge is not authorized. If an unauthorized refill cartridge is detected by the detector 318, the power and control unit 300 may not execute the control algorithm, which may prevent the dispensers from functioning with the unauthorized refill cartridge. Authorization may include one or more levels of authorization, including for example authorization by brand and/or customer. Electronic lock-out features of the present technology may also be configured to permit a refill cartridge to be used only once, allowing the control algorithm to execute upon the first detection of the refill cartridge, but not allowing the control algorithm to execute upon any subsequent detection of the refill cartridge.

Figure 12:
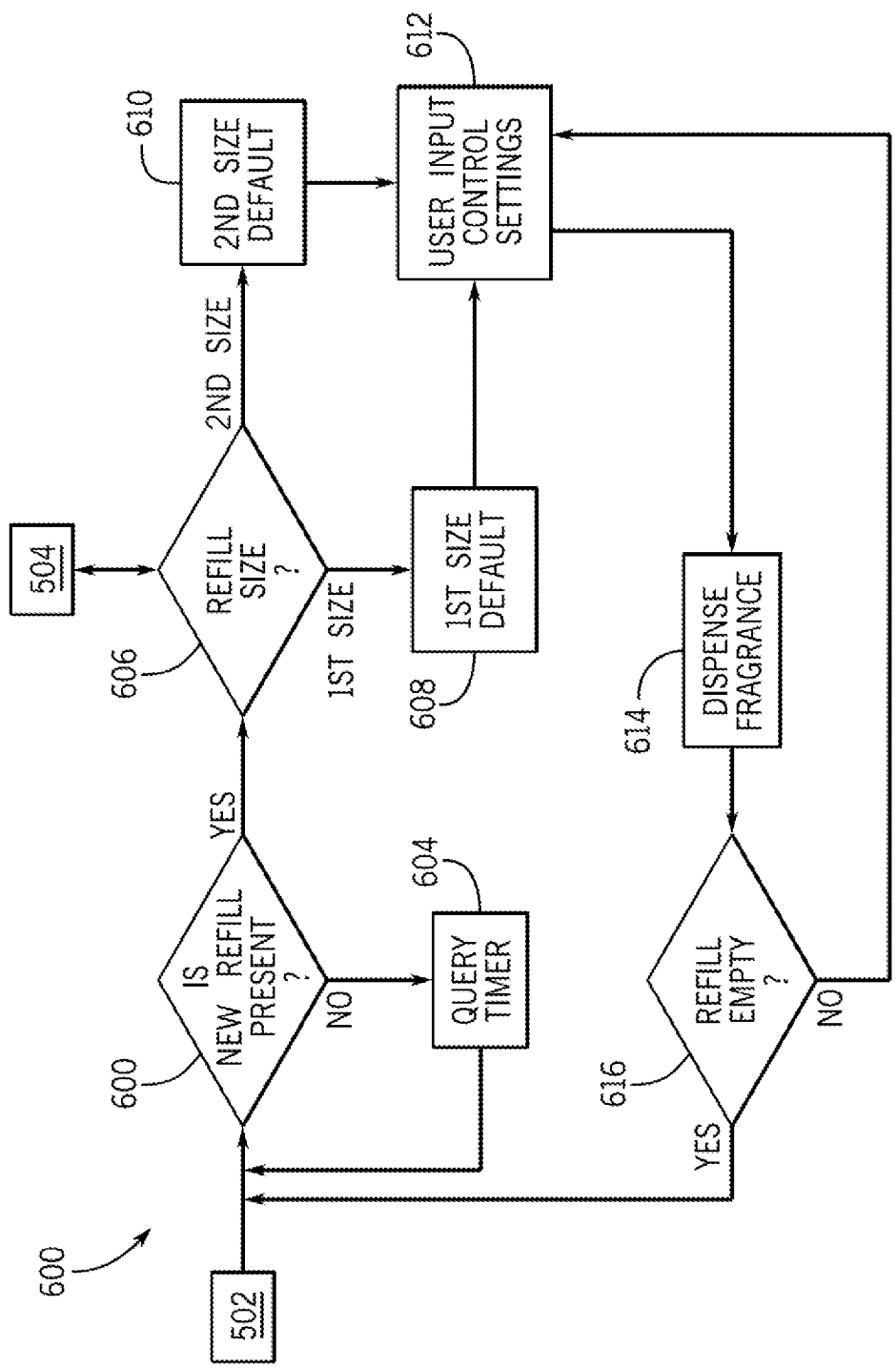
FIG. 12 is a flow diagram of a control algorithm that may be used in a dispenser of FIG. 1.

FIG. 12 is a flow diagram of one example of a control algorithm 600 of the dispenser 100. The control algorithm 600 starts at step 602, where it determines whether a new refill cartridge is present. The control unit 300 may receive a new refill signal from switch 502, indicating that a new refill has been placed, and a refill recognition signal from switch 502 indicating that the refill cartridge is present. If the new refill signal is not received by the control unit, or the refill recognition signal ceases, the control algorithm 600 may proceed to step 604, where a query timer will elapse after a query period, and then the control algorithm 600 will proceed back to step 602 to determine if a refill cartridge is now present. If a new refill has been indicated and is present, the control algorithm 600 will determine that a refill cartridge is present, and may proceed to step 606. At step 606, the control algorithm 600 determines what size the refill cartridge is. The control unit 300 may receive a refill size signal from switch 504 indicating that the refill cartridge has a first size, such as being a small refill cartridge, or that the refill cartridge has a second size, such as being a large refill cartridge. Alternatively, if the control unit 300 receives a refill size signal from switch 504, that may indicate that the refill cartridge has a first size, while the absence of a refill size signal may indicate that the refill cartridge has a second size. The control algorithm 600 may include a first set of default settings that it executes at step 608 when the refill cartridge has a first size, and a second set of default settings that it executes at step 610 when the refill cartridge has a second size. The control algorithm 600 may then proceed from step 608 or step 610 to step 614, in which the control unit causes the dispenser to dispense fragrance based on the set of default settings.

Optionally, the control algorithm 600 may include one or more control settings, which may be entered or changed by input received from a user. In some examples, such input may be provided the by the user through the control display 302, the one or more actuators 304, or the user's personal computing device 316. The one or more control settings may include, for example, the frequency and/or duration of each dispensing action by which the dispenser dispenses substance. Accordingly, instead of proceeding directly to step 614 form step 608 or 610, the control algorithm may proceed to step 612, wherein the set of default settings from step 608 or 610 may be modified to create a modified set of default settings based on the set of default settings and the user input control settings. The control algorithm 600 may then proceed from step 612 to step 614, in which the control unit 300 causes the dispenser to dispense fragrance based on the modified set of default settings.

At step 616, the control algorithm 600 may determine whether the refill cartridge is empty. The determination may be based on the size of the refill, and the control settings, such as dispensing frequency and duration. If the refill cartridge is determined to be empty, the control algorithm may proceed back to step 602, and await placement of a new refill cartridge. If the refill cartridge is determined not to be empty, the control algorithm may proceed back to step 612 to determine whether the user has entered any modifications to the control settings. If a user has modified any control settings, the control algorithm 600 may create a modified set of default settings based on the set of default settings and the user input control settings, and then proceed to step 614. If the user has not modified any control settings, the control algorithm may proceed to step 614.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A dispenser comprising:
   a back housing,
   a front cover connected to the back housing, wherein the front cover has an open position and a closed position relative to the back housing;
   a power and control unit connected to the back housing, the power and control unit comprising at least a control unit,
   a refill housing connected to the back housing, the refill housing being configured to receive a refill cartridge; and
   a switch board positioned between the refill housing and the back housing, the switch board comprising at least one switch operatively connected to the control unit;
   wherein the at least one switch comprises a refill recognition switch configured to send to the control unit at least one of a new refill signal indicating that a new refill cartridge has been inserted into the dispenser and a refill recognition signal indicating that the refill cartridge is present in the refill housing.

2. The dispenser of claim 1, further comprising the refill cartridge, wherein the refill cartridge has a placed position in which the refill cartridge activates the refill recognition switch.

3. The dispenser of claim 2, wherein the refill cartridge comprises a protrusion, and the protrusion of the refill cartridge activates the refill recognition switch when the refill cartridge is in the placed position.

4. The dispenser of claim 2, wherein the refill housing has a refill recognition opening that is aligned with the refill recognition switch, and the protrusion of the refill cartridge extends through the refill recognition opening in the refill housing and activates the refill recognition switch when the refill cartridge is in the placed positon.

5. The dispenser of claim 1, wherein the refill cartridge is either a first refill cartridge having a first size or a second refill cartridge having a second size that differs from the first size, and the refill housing is configurable to receive either the first refill cartridge having a first size or the second refill cartridge having a second size that differs from the first size.

6. A dispenser comprising:
a back housing,
a front cover connected to the back housing, wherein the front cover has an open position and a closed position relative to the back housing;
a power and control unit connected to the back housing, the power and control unit comprising at least a control unit,
a refill housing connected to the back housing, the refill housing being configured to receive a refill cartridge; and
a switch board positioned between the refill housing and the back housing, the switch board comprising at least one switch operatively connected to the control unit;
wherein the refill cartridge is either a first refill cartridge having a first size or a second refill cartridge having a second size that differs from the first size, and the refill housing is configurable to receive either the first refill cartridge having a first size or the second refill cartridge having a second size that differs from the first size; and
wherein the at least one switch comprises a refill size switch configured to send a refill size signal to the control unit indicating a size of the refill cartridge.

7. The dispenser of claim 6, further comprising at least one refill guide removably connected to the refill housing.

8. The dispenser of claim 7, wherein the at least one refill guide has an engaged position in which the at least one refill guide activates the refill size switch.

9. The dispenser of claim 7, wherein the refill housing has a refill guide opening that is aligned with the refill size switch, and the at least one refill guide has an engaged position in which it extends through the refill guide opening in the refill housing and activates the refill size switch.

10. The dispenser of claim 1, wherein the at least one switch further comprises:
a second switch, the second switch being a refill size switch configured to send a refill size signal to the control unit indicating a size of the refill cartridge.

11. The dispenser of claim 1, wherein the dispenser further comprises a lock-out feature.

12. The dispenser of claim 1, wherein the control unit is configured to receive control setting input from a user through at least one of a control display, one or more actuators, and a transceiver configured to send and receive signals from the user's personal computing device.

13. The dispenser of claim 1, wherein the control unit comprises at least one processor and at least one non-volatile memory, and wherein the at least one non-volatile memory stores a dispenser control algorithm that, when executed by the at least one processor, causes the control unit to control operation of the dispenser.

14. The dispenser of claim 13, wherein the control algorithm comprises a first set of default settings that it executes when the refill cartridge has a first size and a second set of default settings that it executes when the refill cartridge has a second size.

15. The dispenser of claim 13, wherein the control algorithm, when executed by the processor, causes the control unit to perform steps comprising:
determining whether a refill cartridge is present;
determining a size of the refill cartridge if the refill cartridge is present, wherein the size of the refill cartridge may be a first size or a second size;
executing a set of default settings, wherein the set of default settings is a first set of default settings when the refill cartridge has the first size and a second set of default settings when the refill cartridge has the second size; and
causing the dispenser to dispense substance.

16. The dispenser of claim 15, wherein the control algorithm, when executed by the processor, causes the control unit to perform a further step comprising:
modifying the set of default settings to create a modified set of default settings based on the set of default settings and user input control settings.

17. The dispenser of claim 16, wherein the step of causing the dispenser to dispense substance is based on the modified set of default settings.

18. A dispenser comprising:
a back housing,
a front cover connected to the back housing, wherein the front cover has an open position and a closed position relative to the back housing;
a power and control unit connected to the back housing, the power and control unit comprising at least a control unit,
a refill housing connected to the back housing, the refill housing being configured to receive a refill cartridge; and
a switch board positioned between the refill housing and the back housing, the switch board comprising a first switch operatively connected to the control unit and a second switch operatively connected to the control unit, the first switch being a refill recognition switch configured to send a refill recognition signal to the control unit indicating that the refill cartridge is present in the refill housing, and the second switch being a refill size switch configured to send a refill size signal to the control unit indicating a size of the refill cartridge.

* * * * *